(12) United States Patent
Woodward et al.

(10) Patent No.: US 7,034,160 B2
(45) Date of Patent: Apr. 25, 2006

(54) CRYSTALLINE FORMS OF A FACTOR XA INHIBITOR

(75) Inventors: Rick G. Woodward, Harleysville, PA (US); David S. Teager, Marcus Hook, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/404,678

(22) Filed: Apr. 1, 2003

(65) Prior Publication Data
US 2003/0225144 A1    Dec. 4, 2003

Related U.S. Application Data

(63) Continuation of application No. PCT/US01/31087, filed on Oct. 4, 2001.

(60) Provisional application No. 60/238,316, filed on Oct. 5, 2000.

(30) Foreign Application Priority Data
Apr. 10, 2001    (GB)    .................................... 0108903

(51) Int. Cl.
*C07D 213/89*    (2006.01)

(52) U.S. Cl. ...................................... 546/332; 514/357
(58) Field of Classification Search ................ 514/351, 514/357; 546/332
See application file for complete search history.

(56) References Cited

U.S. PATENT DOCUMENTS 6,080,767 A * 6/2000 Klein et al. .................. 514/357

FOREIGN PATENT DOCUMENTS

WO    WO 97/24118    7/1997

OTHER PUBLICATIONS

Halebian et al. J of Pharm Sci., (1969), 58, pp. 911-929.*
Chemical & Engineering news, Feb. 2003, pp. 32-35.*
US Pharmacopia, 1995, pp. 1843-1844.*
Concise Encyclopedia Chemistry, pp. 872-873 (1993).*
Brittain et al., Polymorphism in Pharmaceutical Solids, NY: Marcel Dekker, Inc., 1999, pp. 183-226, 228-330.*

* cited by examiner

*Primary Examiner*—Patricia L. Morris
(74) *Attorney, Agent, or Firm*—Joseph D. Rossi (57) ABSTRACT

The present invention relates to novel crystalline forms of an inhibitor of Factor Xa, processes for its preparation, compositions comprising it, and its therapeutic use.

4 Claims, 2 Drawing Sheets

CRYSTALLINE FORMS OF A FACTOR XA INHIBITOR

This application is a continuation application of International Application Number PCT/US01/31087, filed Oct. 4, 2001, which, in turn, is entitled to the benefit of, and claims priority from earlier filed U.S. Application No. 60/238,316, filed Oct. 5, 2000, and Great Britain Application Number 0108903.6, filed Apr. 10, 2001, the contents of all of which are incorporated herein by reference.

FIELD OF THE INVENTION

The present invention relates to novel crystalline forms of an inhibitor of Factor Xa, and its production and use.

BACKGROUND OF THE INVENTION

Factor Xa is the penultimate enzyme in the coagulation cascade. Inhibition of Factor Xa may be achieved, for example, by direct complex formation between a suitable inhibitor and the enzyme and is therefore independent of the plasma co-factor antithrombin III. Effective factor Xa inhibition may be achieved by administering compounds by oral administration, continuous intravenous infusion, bolus intravenous administration or any other suitable route such that it preferably achieves the desired effect of preventing the Factor Xa induced formation of thrombin from prothrombin.

Anticoagulant therapy is often indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels include, for example, acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries.

Chronic anticoagulant therapy may also be beneficial in preventing the vessel luminal narrowing (i.e., restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, or DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition may be characterized by a rapid consumption of coagulation factors and their plasma inhibitors which may result in the formation of life-threatening clots throughout the microvasculature of several organ systems. The indications discussed above include some, but not all, of the possible clinical situations where anticoagulant therapy may be warranted. Those experienced in this field are well aware of the circumstances requiring either acute or chronic prophylactic anticoagulant therapy.

Both free Factor Xa and Factor Xa assembled in the prothrombinase complex (Factor Xa, Factor Va, calcium and phospholipid) may be inhibited by N-[(aminomethyl) phenyl]propyl amide compounds. A particularly promising N-[(aminomethyl) phenyl]propyl amide compound is methyl (2R,3R)-2-{3-[amino(imino)methyl]benzyl}-3-{[4-(1-oxido-4-pyridinyl)benzoyl]amino}butanoate, i.e., the compound of formula (I) (hereinafter referred to as "Compound (I)"):

N-[(aminomethyl) phenyl]propyl amide compounds, including Compound (I), are disclosed in commonly assigned U.S. Pat. No. 6,080,767, which is based on an application that claims priority benefit under 35 U.S.C. § 371 of International application Serial No. PCT/US96/20770 (designating the United States) filed Dec. 23, 1996, which, in turn, claims priority benefit of U.S. Provisional application Ser. No. 60/009,485 filed Jan. 2, 1996.

Treatment and/or prevention of the foregoing pathological conditions may be accomplished by administering a therapeutically effective amount of Compound (I) to a patient in need of such treatment and/or prevention. Treatment with such forms of Compound (I) may be accomplished by its use alone, as an ingredient of a pharmaceutical composition, or in combination with one or more other medications. Compound (I) may be administered enterally or parenterally in solid or liquid dosage forms.

Crystalline forms of Compound (I) have not been known to exist previously. There exists a need for crystalline forms which may exhibit desirable and beneficial chemical and physical properties. There also exists a need for reliable and reproducible methods for the manufacture, purification, and formulation of Compound (I) to permit its feasible commercialization. The present invention is directed to these, as well as other important ends.

SUMMARY OF THE INVENTION

Accordingly, the present invention is directed, in part, to novel crystalline forms of Factor Xa inhibitors. Specifically, in one embodiment, there are provided novel crystalline forms of Compound (I):

in particular in pharmaceutically acceptable form.

These and other aspects of the invention will become more apparent from the following detailed description.

DETAILED DESCRIPTION OF THE INVENTION

The present invention provides, at least in part, crystals of Compound (I) (i.e., methyl (2R,3R)-2-{3-[amino(imino)methyl]benzyl}-3-{[4-(1-oxido-4-pyridinyl)-benzoyl]amino}butanoate) as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) is in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%.

Compound (I) may be present in the novel crystals as the free base or as a salt, solvate and/or hydrate. In accordance with preferred embodiments, Compound (I) is present in the novel crystals as a salt, preferably an acid addition salt. Acids which may be used to prepare the acid addition salts preferably include those which produce, when combined with the free base, pharmaceutically acceptable salts so that the beneficial properties inherent in the free base may not be vitiated by side effects that may be ascribable to the afforded by the acids. Although pharmaceutically acceptable salts of the free base form of Compound (I) are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include, for example, those salts derived from the following acids: mineral acids, such as hydrochloric acid, hydrobromic acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. Preferably, the acid addition salt is derived from a mineral acid, with hydrochloric acid and hydrobromic acid being preferred.

The corresponding acid addition salts comprise the following: hydrochloride, hydrobromide, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The relative amounts of Compound (I) and acid in the acid addition salts may vary and depends, for example, on the particular acid selected and the methods employed in preparing the salts. Preferably, the salts of the present invention comprise about one equivalent of acid for about each equivalent of Compound (I).

The acid addition salts of Compound (I) may be prepared by dissolving the free base in aqueous or aqueous-alcohol solution or other suitable solvents containing the appropriate acid or to which the appropriate acid is added, and isolating the salt by evaporating the solution, or by reacting the free base and acid in an organic solvent, in which case the salt may separate directly and/or may be obtained by concentration of the solution.

In accordance with preferred embodiments of the invention, Compound (I) may be present in the novel crystals as a solvate. A wide variety of solvents may be employed in the preparation of the solvates of Compound (I). Preferred solvents include, for example, polar solvents, including polar protic and polar aprotic solvents. In preferred form, the solvent employed in the preparation of the solvates is selected from the group consisting of alcohols, ethers and nitriles. Suitable alcohols for use in the preparation of solvates of Compound (I) include, for example, methyl alcohol, ethyl alcohol, propyl alcohols, including n-propyl alcohol and i-propyl alcohol, and butyl alcohols, including n-butyl alcohol, t-butyl alcohol, iso-butyl alcohol, and sec-butyl alcohol (i.e., 2-butanol). Preferred among these alcohols are secondary butyl alcohols, with 2-butanol being more preferred. The 2-butanol employed in the solvates may be (R)-(−)-2-butanol, (S)-(+)-2-butanol or mixtures thereof.

Suitable ethers for use in the preparation of solvates of Compound (I) include, for example, dimethoxymethane, tetrahydrofuran, dioxanes, including 1,3-dioxane and 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, and t-butyl methyl ether. Preferred among these ethers are diethyl ether, tetrahydrofuran, and 1,4-dioxane.

A suitable nitrile for use in the preparation of solvates of Compound (I) include, for example, acetonitrile, propionitrile, and butyronitrile. Other solvents suitable for the preparation of solvates of Compound (I), in addition to those exemplified above, would be apparent to one skilled in the art, based on the present disclosure.

The ratio of Compound (I) to solvent in the solvates may vary and depends, for example, on the particular solvent selected and the methods for preparing the solvates. Preferably, the solvates are monosolvates or hemisolvates, with hemisolvates being preferred.

Thus, the present invention is directed, in part, to crystalline forms of the potent Factor Xa inhibitor represented as Compound (I):

(I)

In preferred form, the novel crystals of the present invention comprise methyl (2R,3R)-2-{3-[amino(imino)methyl]benzyl}-3-{[4-(1-oxido-4-pyridinyl)benzoyl]amino}butanoate hydrochloride, 2-butanol hemisolvate, i.e., the compound having Formula (I-i) (hereinafter referred to as "Compound (I-i)"):

(I-i)

where 2-BuOH is 2-butanol. In certain preferred embodiments of the present invention, the 2-BuOH in Compound (I-i) is (S)-(+)-2-butanol. In certain other preferred embodiments, the 2-BuOH in Compound (I-i) is (R)-(−)-2-butanol. In certain other preferred embodiments, the 2-BuOH in Compound (I-i) is a combination of (S)-(+)-2-butanol and (R)-(−)-2-butanol.

Figure 1:
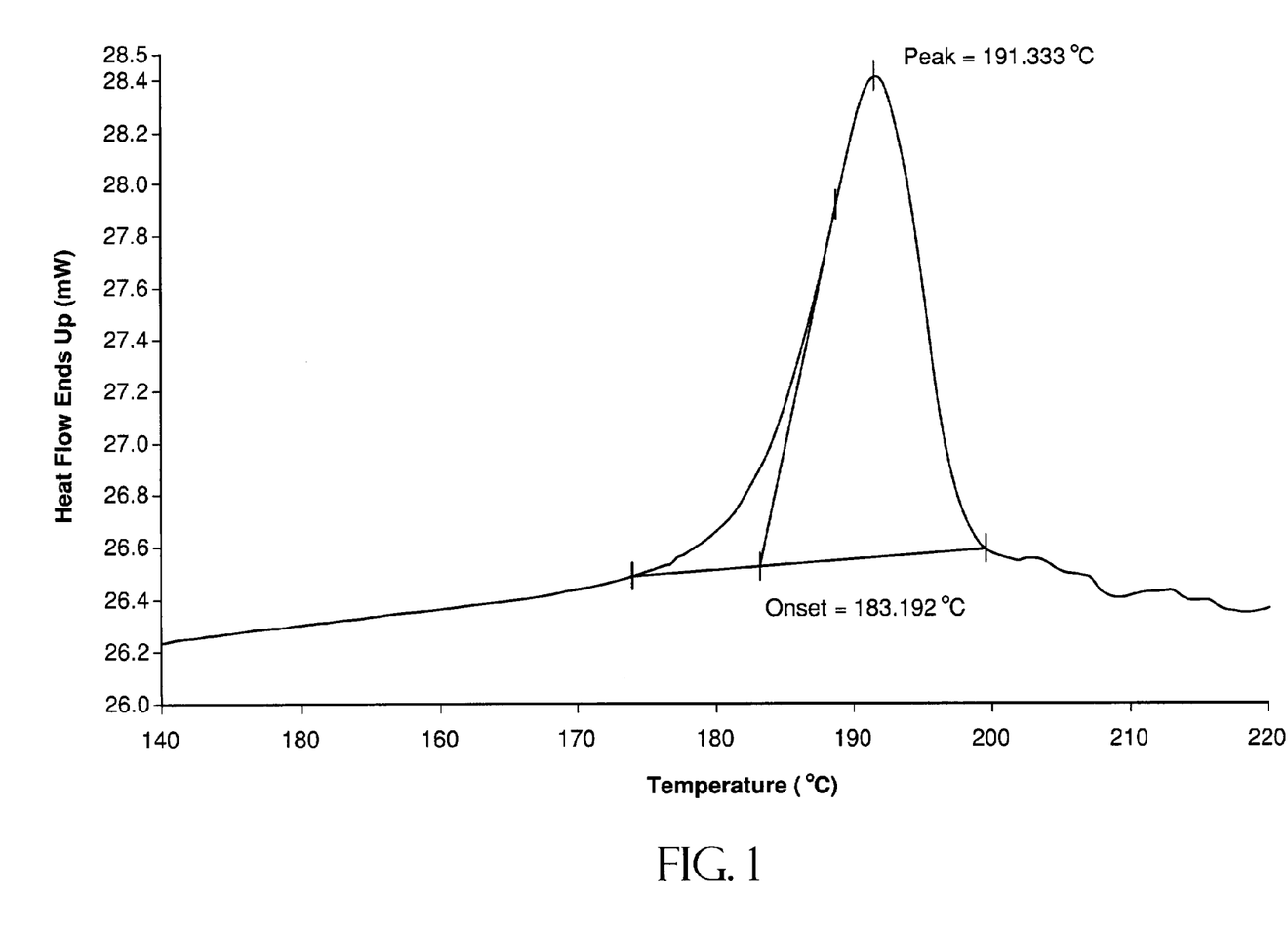
FIG. 1 is a graphical representation of a differential scanning calorimetry thermogram of the 2-butanol hemisolvate of methyl (2R,3R)-2-{3-[amino(imino)methyl]benzyl}-3-{[4-(1-oxido-4-pyridinyl)benzoyl]amino}butanoate hydrochloride.
Figure 2:
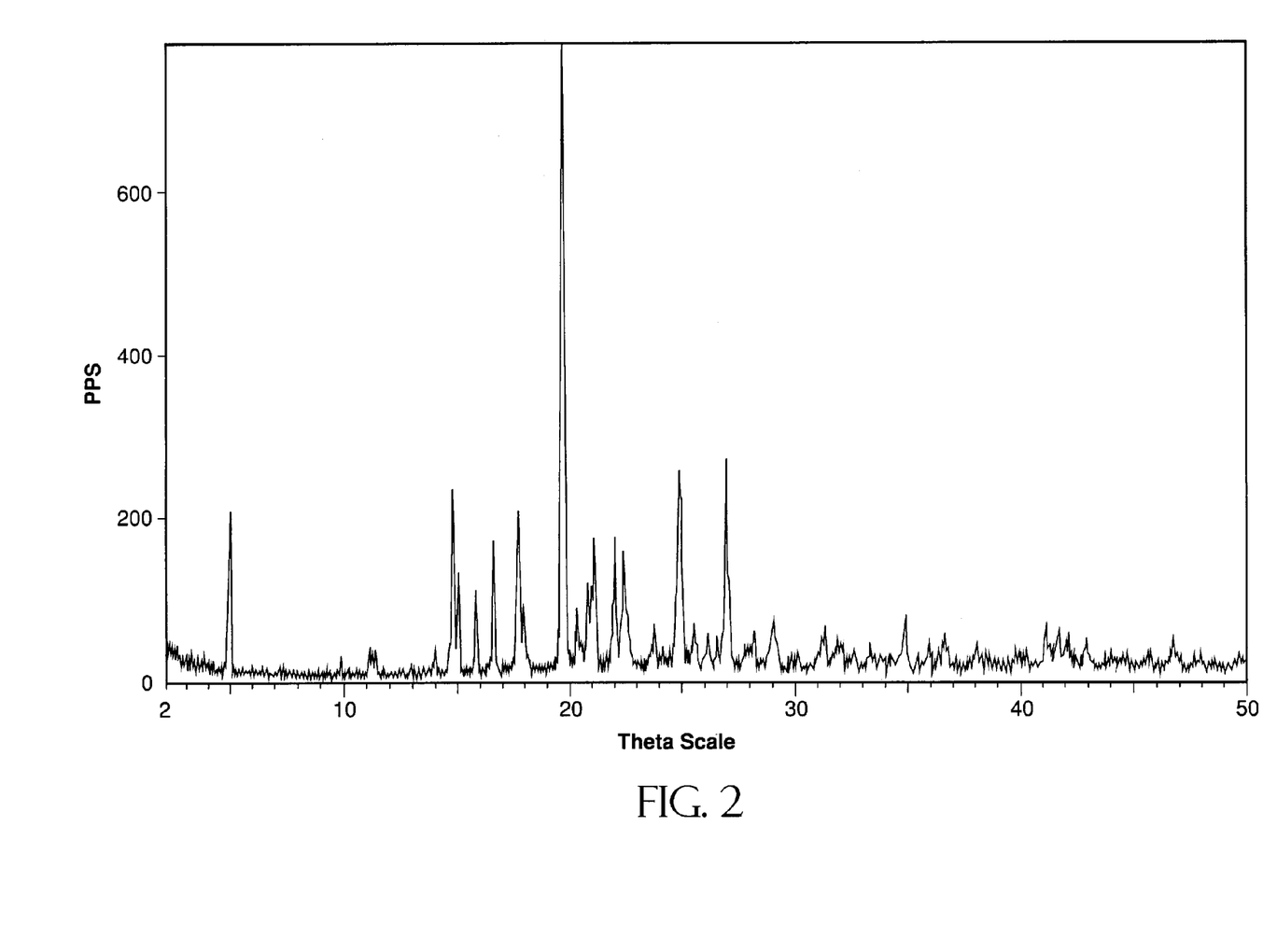
FIG. 2 is a graphical representation of an x-ray powder diffraction pattern of the 2-butanol hemisolvate of methyl (2R,3R)-2-{3-[amino(imino)methyl]benzyl}-3-{[4-(1-oxido-4-pyridinyl)benzoyl]amino}butanoate hydrochloride.

The various forms described herein may be distinguishable from one another through the use of various analytical techniques known to one of ordinary skill in the art. Such techniques include, but are not limited to, chiral or achiral high pressure liquid chromatography (HPLC), x-ray powder diffraction (XRD), differential scanning calorimetry (DSC), and nuclear magnetic resonance (NMR) spectroscopy. In preferred form, Compound (I-i) may be characterized by $^1$H nuclear magnetic resonance spectrum having resonances in DMSO-d6 at 9.6–9.3 (bd, 4H, amidine), 8.55 (d, 1H), 8.38 (d, 2H), 7.96 (2H), 7.8–7.9 (m, 4H), 7.75 (s, 1H), 7.70 (d, 1H), 7.46–7.52 (m, 2H), 4.45 (m, 1H), 4.38 (—OH, 0.5H*), 3.50 (s, 3H), 3.48 (m, 0.5H*), 3.15 (m, 1H), 2.9–3.1 (m, 2H), 1.25–1.35 (m, 1H*) overlapping with 1.29 (d, 3H), 1.0 (d, 1.5H*), 0.8 (t, 1.5H*), wherein * indicates the 2-butanol resonance. Compound (I-i) may be also be characterized by $^{13}$C nuclear magnetic resonance spectrum having resonances in d6-DMSO at 173.0, 165.7, 165.1, 140.6, 139.0 (2C), 138.0, 135.2, 134.4, 134.0, 128.9, 128.4, 128.2 (2C), 127.8, 126.0 (2C), 125.97, 123.9 (2C), 67.1 (*), 51.8, 51.5, 46.6, 33.3, 31.7 (*), 23.0 (*), 17.5, 10.0 (*), wherein * indicates the 2-butanol resonance. Compound (I-i) may also be characterized by a differential scanning calorimetry thermogram having an onset peak at about 175° C. to about 185° C., preferably about 181.0° C. to 184° C., and a peak at about 185° C. to about 192° C. Compound (I-i) may also be characterized by an x-ray powder diffraction pattern which comprises two or more 2θ values selected from 5.0±0.2, 14.8± 0.2, 15.1±0.2, 15.8±0.2, 16.6±0.2, 17.7±0.2, 17.9±0.2, 19.6±0.2, 24.9±0.2, 25.0±0.2, and 27.0±0.2.

Broadly speaking, the novel crystalline forms of Compound (I) may be prepared by a variety of methods, including but not limited to, recrystallizing Compound (I), preferably in salt form, from a suitable solvent. More preferably, the crystalline form of Compound (I) is obtained directly from a reaction mixture through the addition of a suitable solvent. In certain preferred embodiments, Compound (I) is obtained through either recrystallization or solvent addition using a solvent which is to be incorporated in the solvate. Suitable solvents include those mentioned above in connection with the solvates.

Compound (I) may be prepared using methods well known to the skilled artisan of organic synthesis, as well as methods taught in commonly assigned U.S. Pat. No. 6,080, 767, which claims priority benefit under 35 U.S.C. § 371 of International Application Serial No. PCT/US96/20770 (designating the United States) filed Dec. 23, 1996, which, in turn, claims priority benefit of U.S. Provisional Patent Application Ser. No. 60/009,485 filed Jan. 2, 1996. The disclosures of each of these documents are hereby incorporated herein by reference, in their entireties.

A particularly preferred novel crystalline form of Compound (I) is the 2-butanol hemisolvate hydrochloride salt, referred to herein as Compound (I-i). Compound (I-i), as well as other crystalline forms, may be prepared by the methods described in Scheme 1. Once the target compound is made, crystalline forms of Compound (I) may be obtained by recrystallization of the crude, amorphous product or, alternatively, by addition of a suitable solvent following the final chemical step of the synthetic process.

Scheme 1

In the above reaction scheme, "TsOH" means p-toluenesulfonic acid, "LHDMS" means lithium hexamethyldisilazide, "THF" means tetrahydrofuran, "TBTU" means O-(1H-benzotriazol-1-yl)-N,N,N',N'-tetramethyluronium tetrafluoroborate, "NMM" means N-methyl morpholine, "DMF" means N,N-dimethylformamide, "MMPP" means magnesium monoperoxyphthalate, and "MeOH" means methanol.

Compound (II) may be prepared using methods well known to the skilled artisan of organic synthesis, as well as methods taught in commonly assigned U.S. patent application Ser. No. 09/491,548, filed Jan. 26, 2000, which is a continuation of International Patent Application No. PCT/US99/30366, filed Dec. 17, 1999, which is, in turn, a continuation-in-part of U.S. Patent Application Ser. No. 60/114,598, filed Dec. 31, 1998, now abandoned. The disclosures of each of these documents are hereby incorporated herein by reference, in their entireties.

Procedures for recrystallization of the preferred crystalline forms of Compound (1) will be readily understood by one skilled in the art, once placed in possession of the present disclosure. By way of general guidance, Compound (I) may be suspended and/or stirred in a suitable solvent to afford a slurry, which may be heated to promote dissolution. The term "slurry", as used herein, means a saturated solution of Compound (I), which may also contain an additional amount of Compound (I) to afford a heterogeneous mixture of Compound (I) and a solvent at a given temperature. Suitable solvents in this regard include, for example, halogenated solvents, hydrocarbon solvents, ether solvents, polar protic solvents, and polar aprotic solvents, and mixtures of two or more of these.

Suitable halogenated solvents include, for example, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, for example, benzene, cyclohexane, pentane, hexane, toluene, cycloheptane, methylcyclohexane, heptane, ethylbenzene, m-, o-, or p-xylene, octane, indane and nonane.

Suitable ether solvents include, for example, dimethoxymethane, tetrahydrofuran, dioxanes, including 1,3-dioxane and 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, and t-butyl methyl ether.

Suitable polar protic solvents include, for example, alcohols and glycols, such as methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable polar aprotic solvents include, for example, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, dioxane, sulfolane, N,N-dimethylpropionamide, nitromethane, nitrobenzene and hexamethylphosphoramide. Other solvents suitable for the preparation of slurries of Compound (I), in addition to those exemplified above, would be apparent to one skilled in the art, based on the present disclosure.

If the desired crystalline form is a solvate or hemisolvate, preferred solvents include those which may be complementary to the desired solvate, i.e., solvents which may be ultimately present in the crystalline lattice itself. Preferred among these solvents are the alcohol and ether solvents discussed above, with alcohols being preferred. These include, but are not limited to, alcohol solvents such as methyl alcohol, ethyl alcohol, propyl alcohol, including n-propyl alcohol and i-propyl alcohol, and butyl alcohol, including n-butyl alcohol, t-butyl alcohol, iso-butyl alcohol, and sec-butyl alcohol (i.e., 2-butanol). More preferred among these solvents are secondary butyl alcohols, with 2-butanol, including the R- and S-forms thereof, being even more preferred. In the case of alcholic solvents, a cosolvent, such as water, may be used, if necessary or desired, to aid in dissolution. It will be appreciated that the amount of such cosolvent employed may vary and depends on desired yield, purity, and other concerns. By way of general guidance about 1% of cosolvent may be used based on the amount of solvent used in the recrystallization.

The amount of solvent employed in the recrystallization may vary and depends, for example, on the particular solvent employed, as well as the form of Compound (I), for example, free base or acid addition salt. Broadly speaking, the amount of solvent employed in the recrystallization may range from about 1 mL solvent per gram Compound (I) to about 50 mL solvent per gram Compound (I), and all combinations and subcombinations of ranges and specific amounts of solvent therein. In preferred form, the amount of solvent employed may be from about 3 mL solvent per gram Compound (I) to about 10 mL solvent per gram Compound (I).

As noted above, the combination of solvent and Compound (I) may be heated for more effective dissolution of the compound in the solvent, as well as improved conversion to the preferred crystalline form. Preferred temperatures in this regard may range from about 30° C. to about the boiling point (i.e., the reflux temperature) of the involved solvent, and all combinations and subcombinations of ranges and specific temperatures therein. More preferred temperatures may range from about 60° C. to about the boiling point of the solvent. By way of example, heating 1 gram of a salt of Compound (I), preferably the HCl salt, in about 6 mL 2-butanol at about 85° C. to about 90° C. results in substantially complete dissolution of Compound (I). Cosolvents, such as water, may be removed azeotropically, preferably until crystallization occurs spontaneously. The resulting mixture of solvent and Compound (I) may be cooled to initiate and/or continue crystallization. The mixture may be preferably cooled to a temperature which ranges from about −20° C. to about 20° C., and all combinations and subcombinations of ranges and specific temperatures therein.

Seed crystals may be added to any crystallization mixture to promote crystallization. As will be clear to the skilled artisan, seeding is used as a means of controlling growth of a particular polymorph or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nývlt, *Chemical Engineering Science*, 1971, 26, 369–377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e. change to amorphous or to another polymorph).

The cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as NMR, DSC, XRD, HPLC, or the like, to assure formation of the preferred crystalline form of the product. The resulting crystalline form is typically produced in an amount of greater than about 70% isolated yield, but preferably greater than 90% based on the amount of Compound (I) originally employed in the crystallization procedure. The product may be comilled or passed through a mesh screen to delump the product, if necessary.

Preferred crystalline forms may also be prepared directly from the reaction medium of the final process step for preparing Compound (I). This may be achieved, for example, by employing in the final process step a solvent or mixture of solvents from which Compound (I) may be crystallized. Alternatively, preferred crystalline forms may be obtained by distillation or solvent addition techniques which would be apparent to the skilled artisan, once placed in possession of the present disclosure. Preferably, such techniques may be carried out following the final process step for preparing Compound (I) through the addition of a solvent suitable for isolating the product in crystalline form. Suitable solvents for this purpose include any of those solvents described herein.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like, by way of general guidance, the reaction solution may be distilled to about $\frac{1}{10}$ the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

Solvent exchange may be accomplished through the addition of the desired replacement solvent. If the desired crystalline form is a solvate or hemisolvate, preferred solvents include those which are complementary to the desired solvate, i.e., solvents which may ultimately participate in the crystalline lattice itself. Even more preferred solvents include the polar solvents discussed above, including alcohols, preferably secondary alcohols, ethers and the like. The solvent is typically added to provide a desired concentration such that Compound (I) substantially completely dissolves.

The solution may be filtered and washed to remove additional impurities or salts which may have precipitated during solvent replacement, followed by the combination of the filtrates. The solution may be further distilled to remove as much reaction solvent as is practicable. The use of additional recrystallization solvent may be necessary for continued distillation as is well understood by the skilled artisan, once armed with the present disclosure.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of (I) in solution is preferably about 4% to about 7%. More preferred is about 4% to 6% (I) in 1:6 MeOH:crystallization solvent. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

Following crystallization, the mixture may be preferably cooled to a temperature ranging from about −20° C. to about 20° C., and all combinations and subcombinations of ranges and specific temperatures therein. The resulting solid may be filtered under vacuum, washed with a suitable solvent, such as cold recrystallization solvent, and dried under a nitrogen purge to afford the desired crystalline form. The solids may be analyzed using suitable analytical techniques, including NMR, DSC, XRD, and HPLC as discussed above. The resulting crystalline form is typically produced in about 70% isolated yield. The product may be comilled or passed through a mesh screen to delump the product.

The novel crystalline forms of Compound (I) described herein may be formulated into pharmaceutical compositions and/or employed in therapeutic and/or prophylactic methods. These methods include, but are not limited to, the administration of the novel crystalline compound (I), alone or in combination with one or more other pharmaceutically active agents, including agents that may be useful in the treatment of the disorders mentioned herein. If Compound (I) is used in combination with another medication, the combination of compounds described herein may result in a synergistic combination. Synergy, as described for example by Chou and Talalay, Adv. Enzyme Regul. 22:27–55 (1984), occurs when the effect of the compounds when administered in combination is greater than the additive effect of the compounds when administered alone as a single agent. In general, a synergistic effect is most clearly demonstrated at suboptimal concentrations of the compounds.

The compounds and pharmaceutical compositions of the present invention may be useful in inhibiting Factor Xa. Accordingly, the present invention provides methods for the treatment and/or prevention of a pathological condition that may be capable of being modulated by inhibiting production of Factor Xa. The term "pathological condition", as used herein, refers to diseases, disorders and/or conditions in a patient, particularly those in which Factor Xa may play a role. The term "patient", as used herein, refers to animals, including mammals, preferably humans. Examples of pathological conditions that may be capable of being treated with the compounds and compositions of the present invention include, for example, acute myocardial infarction (AMI), unstable angina, thromboembolism, acute vessel closure associated with thrombolytic therapy, percutaneous transluminal coronary angioplasty (PTCA), transient ischemic attacks, stroke, intermittent claudication, and restenosis.

The crystalline forms of Compound (I) described herein thus may be useful for, inter alia, inhibiting blood coagulation by virtue of their general ability to inhibit the penultimate enzyme in the coagulation cascade, Factor Xa, rather than thrombin. Novel crystalline forms of Compound (I) within the scope of the present invention may exhibit marked pharmacological activities according to tests described in the literature, including in vivo tests and in vitro tests, the latter of which are believed to correlate to pharmacological activity in humans and other mammals. For example, both free Factor Xa and Factor Xa assembled in the prothrombinase complex (Factor Xa, Factor Va, calcium and phospholipid) may be inhibited. Factor Xa inhibition may be obtained by direct complex formation between the inhibitor and the enzyme and is therefore independent of the plasma co-factor antithrombin III. Effective Factor Xa inhibition may be achieved by administering Compound (I) by oral administration, continuous intravenous infusion, bolus intravenous administration or any other suitable route such that it may achieve the desired effect of preventing the Factor Xa induced formation of thrombin from prothrombin.

In addition to their use in anticoagulant therapy, Factor Xa inhibitors may be useful in the treatment or prevention of other diseases in which the generation of thrombin may play a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of Factor Xa may effectively block thrombin generation and therefore neutralize any pathologic effects of thrombin on various cell types.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The novel crystalline forms of Compound (I) may be administered to a patient, for example, enterally or parenterally. The percentage of active ingredient in the pharmaceutical compositions of the present invention may vary, it being only necessary that it should constitute a proportion such that a suitable dosage shall be obtained. Obviously, several unit dosage forms may be administered at about the same time. The dose employed may be determined by the physician, and may depend upon the desired therapeutic effect, the route of administration and the duration of the treatment, and the condition of the patient. The dosage of the novel form of Compound (I) that will be most suitable for prophylaxis or treatment may vary with the form of administration, the particular novel form of the compound chosen and the physiological characteristics of the particular patient under treatment. Broadly, small dosages may be used initially and, if necessary, increased by small increments until the desired effect under the circumstances is reached.

Generally speaking, in the adult, suitable doses may range from about 0.01 to about 100 mg/Kg body weight, and all combinations and subcombinations of ranges and specific doses therein. Preferred doses may be from about 0.01 to about 10 mg/kg body weight per day by inhalation, from about 0.01 to about 100, preferably 0.1 to 70, more preferably 0.5 to 10 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product.

The products according to the invention may be administered as frequently as necessary to obtain the desired therapeutic effect. Some patients may respond rapidly to a higher or lower dose and may find much weaker maintenance doses adequate. For other patients, it may be necessary to have long-term treatments at the rate of about 1 to about 4 doses per day, in accordance with the physiological requirements of each particular patient. Generally, the active product may be administered orally about 1 to about 4 times per day. It goes without saying that, for other patients, it may be necessary to prescribe not more than one or two doses per day.

The crystalline and solvate forms of Compound (I) of this invention may be administered in oral dosage forms such as tablets, capsules (each of which includes sustained release or timed release formulations), pills, powders, granules, elixirs, tinctures, suspensions, syrups, and emulsions. Solid dosage forms (pharmaceutical compositions) suitable for administration may generally contain from about 1 mg to about 1000 mg of Compound (I) per dosage unit.

For oral administration in solid form such as a tablet or capsule, the novel crystals of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients." These excipients include, among others, diluents, binders, lubricants, glidants and disintegrants. Coloring agents may also be incorporated. "Diluents" as used herein, refers to agents which may impart bulk to the formulation to make a tablet a practical size for compression. Examples of diluents are lactose and cellulose. "Binders" as used herein, refers to agents that may be used to impart cohesive qualities to the powered material to help ensure the tablet remains intact after compression, as well as to improve the free-flowing qualities of the powder. Examples of typical binders include lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may can result in a formulation with reduced disintegration and/or delayed dissolution of the drug substance. "Glidants", as used herein, refers to substances which may improve the flow characteristics of the granulation material. Examples of glidants include talc and colloidal silicon dioxide. "Disintegrants", as used herein, refer to substances or mixtures of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

For oral administration in liquid form, the solvate or crystalline Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccharin, aspartame, etc. If sugar substitutes are selected as the sweetening agent, the amount employed in the compositions of the invention may be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used may range from about 200 to less than about 325 mesh US Standard Screen, and all combinations and subcombinations of ranges and specific particle sizes therein.

Sterile injectable solutions may be prepared by incorporating novel crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

Liquid compositions may also contain other components routinely utilized in formulating pharmaceutical compositions. One example of such components is lecithin. Its use in compositions of the invention as an emulsifying agent may range from about 0.05 to about 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The solvate of crystalline Compound (I) may also be coupled with soluble polymers as targetable drug carriers. Such polymers can include, for example, polyvinylpyrrolidine pyran copolymer, polyhydroxypropylmethacrylamidephenol, polyhydroxyethyl-aspartamidephenol or polyethylene oxide-polylysine substituted with palmitolyl residues. Furthermore, crystalline Compound (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of the solvate or crystalline Compound (I) may contain the solvate or crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols may be suitable carriers for parenteral solutions. Solutions for parenteral solutions may be prepared by dissolving the solvate or crystalline Compound (I) in the carrier and, if necessary, adding buffering substances. Anti-oxidizing agents, such as sodium bisulfite, sodium sulfite, or ascorbic acid either alone or combined, may be suitable stabilizing agents. Citric acid and its salts and sodium EDTA may also be employed. Parenteral solutions may also contain preservatives, such as benzalkonium chluoride, methyl- or propyl-paraben and chlorobutanol.

Suitable pharmaceutical carriers, excipients and diluents are described in Remington's Pharmaceutical Sciences, Mack Publishing Co., the disclosures of which are hereby incorporated herein by reference, in their entireties. Useful pharmaceutical dosage-forms for administration of the compounds of this invention can be illustrated as follows:

Capsules

A large number of unit capsules may be prepared by filling standard two-piece hard gelatin capsules each with 100 mg of powdered active ingredient (i.e., Factor Xa inhibitor), 150 mg of lactose, 50 mg of cellulose, and 6 mg of magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 mg of the active ingredient. The capsules may then be washed and dried.

Tablets

A large number of tablets may be prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Suspensions

An aqueous suspension may be prepared for oral administration so that each 5 mL contains 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection may be prepared by stirring 1.5% by weight of active ingredient in 10% by volume propylene glycol and water. The solution may be sterilized by commonly used techniques.

Nasal Spray

An aqueous solution may be prepared such that each mL contains 10 mg of active ingredient, 1.8 mg methylparaben, 0.2 mg propylparaben and 10 mg methylcellulose. The solution may be dispensed into 1 mL vials.

Lung Inhaler

A homogeneous mixture of the active ingredient in polysorbate 80 may be prepared such that the final concentration of the active ingredient will be 10 mg per container and the final concentration of polysorbate 80 in the container will be 1% by weight. The mixture may be dispensed into each can, the valves may be crimped on the can and the required amount of propellant, for example, dichlorotetrafluoroethane, may be added under pressure.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Thus, Compound (I) may be used alone or in combination with other diagnostic, anticoagulant, antiplatelet, fibrinolytic, antithrombotic and/or profibrinolytic agents. For example adjunctive administration of Factor Xa inhibitors with standard heparin, low molecular weight heparin, direct thrombin inhibitors (i.e. hirudin), aspirin, fibrinogen receptor antagonists, streptokinase, urokinase and/or tissue plasminogen activator may result in improved antithrombotic or thrombolytic efficacy or efficiency. The novel crystals described herein may be administered to treat thrombotic complications in a variety of animals, such as primates, including humans, sheep, horses, cattle, pigs, dogs, rats and mice. Inhibition of Factor Xa may be useful not only in the anticoagulant therapy of individuals having thrombotic conditions, but also when inhibition of blood coagulation may be required, such as to prevent coagulation of stored whole blood and to prevent coagulation in other biological samples for testing or storage. Thus, any Factor Xa inhibitor, including the novel crystalline forms of Compound (I) as described herein, can be added to or contacted with any medium containing or suspected of containing Factor Xa and in which it may be desired to inhibit blood coagulation.

The novel crystals of the present invention may be used in combination with any antihypertensive agent or cholesterol or lipid regulating agent, or concurrently in the treatment of restenosis, atherosclerosis or high blood pressure. Some examples of agents that may be useful in combination with a novel form of Compound (I) according to the present invention in the treatment of high blood pressure include, for example, compounds of the following classes: beta-blockers, ACE inhibitors, calcium channel antagonists and alpha-receptor antagonists. Some examples of agents that may be useful in combination with a compound according to the invention in the treatment of elevated cholesterol levels or disregulated lipid levels include compounds known to be HMGCoA reductase inhibitors, or compounds of the fibrate class.

Accordingly, components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, these agents may be administered together or in any order. When not administered at the same time, preferably the administration of component (a) and (b) occurs less than about one hour apart. Preferably, the route of administration of component (a) and (b) is oral. Although it may be preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

The present invention is further described in the following examples. All of the examples are actual examples. These examples are not to be construed as limiting the scope of the appended claims.

EXAMPLES

Example 1

Preparation of Compound (III)

(II)

1. LHMDS, THF, -20° C.
2. Br—C6H4—CN
3. C6H5CO2H
   water/toluene

-continued (III)

To a reactor were charged Compound (II) (100.0 g) and anhydrous THF (320 g). The resulting suspension was cooled down to −20±3° C. and LiHMDS (475.6 grams, 1.3 M solution in THF) was added over 55 minutes and stirred for 20 minutes at −20±3° C. A solution of α-bromo-m-tolunitrile in THF (65.1 g in 181 g of THF) was then charged into the reactor over 40 minutes while maintaining the temperature at −20±3° C. and stirred for another 30 minutes. Benzoic acid (126.6 grams) was charged as a solid to the reactor. Water (1000 g) was then added and mixture distilled at a 65±3° C. jacket temperature and 200–233 mbar vacuum. After distilling to a constant pot temperature of 57° C. and constant head temperature of 45° C., the distillation was stopped. Toluene (432 g) was added to the hot solution and stirred while cooling down to 10±2° C. The resulting suspension was then filtered and the filter cake washed with water (250 grams) and toluene (432 grams). Compound (III) was dried at 45–50° C. at ~350 mbar vacuum under a nitrogen stream for 24 hours until constant weight. The isolated solid weighed 76.0 grams (62.0% yield).

Example 2

Preparation of Compound (V)

(III)

1. aq. Na2CO3
2. (IV)
3. TBTU
   NMM, DMF

(V)

Compound (III) was partitioned between dichloromethane and aqueous sodium carbonate. The organic phase (containing the free base of (III)) was washed with additional aqueous sodium carbonate and was distilled under reduced pressure and solvent exchanged with dimethylformamide (DMF). This solution was assayed for wt/wt content of (III). To a suspension of (IV) (1.0 equivalent vs. (III)) in DMF were added 2 equivalents of 4-methylmorpholine and 1.1 equivalents of O-Benztriazol-1-yl-N,N,N',N'-tetramethyluronium tetrafluoroborate (TBTU). This mixture was stirred at ambient temperature until ester activation was complete (about 90 minutes). The DMF solution of Compound (III) (1 equivalent) was added and the resulting solution stirred overnight after which HPLC indicated that the reaction was complete. Water was added at 75° C. and the mixture was cooled to crystallize the product. The mixture was cooled to 5° C., filtered, and the filter cake was washed with water. The product was dried under reduced pressure at 70° C.

Example 3

Preparation of Compound (VI)

In a well-stirred reactor, 45 g of Compound (V) in 450 mL dichloromethane was reacted for at least 5 hours with 61 g of magnesium monoperoxyphthalate (66.4% based on available oxygen, 1.5 eq.) in 450 g of water until the reaction was complete. The phases were separated and the organic phase was washed successively with equal volumes of water, a 5% aqueous sodium bicarbonate solution, and water. The resulting solution was concentrated to an approximately 40 wt % solution and diluted with 180 g of methyl isobutyl ketone (MIBK). Further distillation to remove residual dichloromethane, seeding with appropriate crystals, and cooling gave the product as a crystalline solid. The crystals were filtered, rinsed with 30 g of MIBK, and dried at 50° C. under reduced pressure to give 41.8 g of Compound (VI) (89.3% yield).

Example 4

Preparation of Compound (I)

To a 200-mL jacketed reaction flask were charged Compound (VI) (50.0 g, 116 mmol) and methanol (50 mL). This mixture was cooled to −5° C. and sealed after establishing a partial vacuum (ca. 100 torr). Anhydrous HCl (52.2 g, 1.43 mol) was added while maintaining the reaction temperature at less than 0° C. The reaction was stirred at 0±1° C. under closed conditions. After 16 hours, the reaction was complete (less than 2 A % (VI) by HPLC). To the intermediate product solution was added anhydrous methanol (100 mL) while maintaining the temperature at less than 5° C. The solution was treated with $NH_3$ (27.7 g, 1.62 mol) keeping the temperature less than 0° C. Before allowing the mixture to warm to room temperature, a pH check was made of an aliquot dissolved in DI water (a pH of 8–10 indicates a sufficient charge of ammonia). The reaction was stirred at 20° C. overnight at which point the reaction was complete.

Example 5

Preparation of Compound (I-i) by Solvent Addition (I-i)

To the ammonium chloride slurry from Example 4 was added 2-butanol (840 mL), and the resulting mixture was stirred for 1 hour while warming to 70° C. The ammonium chloride was removed by hot filtration and the cake was washed with a solution of 20 mL methanol in 160 mL 2-butanol. The filtrates were combined and 0.5 g of seed crystals were added. The mixture was allowed to stir overnight at ambient temperature. The slurry was cooled to −15° C. and held for 2 hours to ensure complete crystallization. The solid was filtered and the reactor and cake were washed with 165 mL of 2-butanol. The solid was dried under vacuum at 45–50 C with a nitrogen bleed giving 44.3 g (73.2%) of Compound (I-i) as an off-white crystalline solid.

Example 6

Preparation of Compound (I-i) by Solvent Replacement

After carrying out the synthesis of Compound (I), as set forth above in Example 4, ammonium chloride was removed from the reaction mixture by filtration and the resulting filter cake was washed with anhyrous methanol. The resulting solution was concentrated to remove methanol and residual ammonia to approximately 1/10 the original reaction volume. The reaction mixture was sampled and assayed for wt % of Compound (I). Methanol was added to adjust the final concentration to 50 wt % of Compound (I). To the resulting slurry was added 2-butanol and the mixture was stirred for one hour. The precipitated ammonium chloride was washed with a solution of methanol and 2-butanol. The filtrates were combined and further concentrated, and additional 2-butanol was added until the methanol was reduced to a low level. The overhead temperature during the distillation was about 98° C. Seed crystals were added to initiate crystallization. The mixture was allowed to cool to 20° C. over 2 hours and was maintained at that temperature for 2 hours to ensure complete crystallization. The solids were isolated by filtration, and the reactor and filter cake were washed two times with 2-butanol. The solids were dried in a vacuum oven at 50 to 60° C. to give Compound (I-i) as an off-white solid in 70% yield.

Example 7

Preparation of Compound (I-i) through Recrystallization

Compound (I) (50 g) as an amorphous hydrochloride salt (water content 1.2 wt %) was suspended in 2-butanol (300 g) containing water (3 g). The mixture was heated to boiling and dissolution occurred at about 85° C. to 90° C. The sample was concentrated slightly to azeotropically remove the water and crystallization began to occur spontaneously. The resulting mixture was cooled to continue crystallization. The crystals were filtered, washed with 2-butanol, and dried overnight at 20 p.s.i. vacuum with a nitrogen purge at 60° C. The dried crystals of Compound (I-i) weighed 48.3 grams (91% yield).

Physical Data of Compound (I-i)

$^1$H NMR (DMSO-d6) 9.6–9.3 (bd, 4H, amidine), 8.55 (d, 1H), 8.38 (d, 2H), 7.96 (2H), 7.8–7.9 (m, 4H), 7.75 (s, 1H), 7.70 (d, 1H), 7.46–7.52 (m, 2H), 4.45 (m, 1H), 4.38 (—OH, 0.5H*), 3.50 (s, 3H), 3.48 (m, 0.5H*), 3.15 (m, 1H), 2.9–3.1 (m, 2H), 1.25–1.35 (m, 1H*) overlapping with 1.29 (d, 3H), 1.0 (d, 1.5H*), 0.8 (t, 1.5H*), wherein * indicates the 2-butanol resonance.

$^{13}$C NMR (d6-DMSO) at: 173.0, 165.7, 165.1, 140.6, 139.0 (2C), 138.0, 135.2, 134.4, 134.0, 128.9, 128.4, 128.2 (2C), 127.8, 126.0 (2C), 125.97, 123.9 (2C), 67.1 (*), 51.8, 51.5, 46.6, 33.3, 31.7 (*), 23.0 (*), 17.5, 10.0 (*), wherein * indicates the 2-butanol resonance.

Differential Scanning Calorimetry (DSC) (heating from 25.0° C. to 220.0° C. at 10.0° C./min.): Batch 1: onset peak at 176.4° C., peak at 185.3° C., and an endotherm of about 76 J/g; Batch 2: onset peak at 183.2° C., peak at 191.3° C., and an endotherm of 101.9 J/g.

X-ray powder diffraction (XRD): 2θ values at 5.0, 14.8, 15.1, 15.8, 16.6, 17.7, 17.9, 19.6, 24.9, 25.0, and 27.0.

Elemental analysis: Calculated: C 62.36%, H 6.20%, N 10.77%, Cl 6.82% Found: C 62.33%, H 6.19%, N 10.64%, Cl 6.70% Mass spec: ion spray found M+ at 477

The disclosures of each patent, patent application and publication cited or described in this document are hereby incorporated herein by reference, in their entirety. As will be apparent to those skilled in the art from the foregoing description, various modification of the invention, in addition to those described herein, are also intended to fall within the scope of the appended claims.

What is claimed is:

1. A crystalline form of (2R,3R)-2-{3-[amino(imino)methyl]benzyl}-3-{[4-(1-oxido-4-pyridinyl)benzoyl]amino}butanoate hydrochloride, 2-butanol hemisolvate according to the formula 2. The crystalline form of claim 1 having an x-ray powder diffraction pattern which comprises two or more 2θ values selected from 5.0±0.2, 14.8±0.2, 15.1±0.2, 15.8±0.2, 16.6±0.2, 17.7±0.2, 17.9±0.2, 19.6±0.2, 24.9±0.2, 25.0±0.2, and 27.0±0.2.

3. The crystalline form according to claim 1 wherein 2-BuOH is (S)-(+)-2-butanol.

4. The crystalline form according to claim 1, wherein 2-BuOH is (R)-(−)-2-butanol.

* * * * *